US006599627B2

United States Patent
Yeo et al.

(10) Patent No.: US 6,599,627 B2
(45) Date of Patent: Jul. 29, 2003

(54) MICROENCAPSULATION OF DRUGS BY SOLVENT EXCHANGE

(75) Inventors: Yoon Yeo, Lafayette, IN (US); Alvin Un-Teh Chen, West Lafayette, IN (US); Osman A. Basaran, West Lafayette, IN (US); Kinam Park, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 10/017,338

(22) Filed: Dec. 13, 2001

(65) Prior Publication Data

US 2002/0160109 A1 Oct. 31, 2002

Related U.S. Application Data

(60) Provisional application No. 60/254,920, filed on Dec. 13, 2000, and provisional application No. 60/294,263, filed on May 31, 2001.

(51) Int. Cl.$^7$ ............................ B32B 15/02; B01J 13/02
(52) U.S. Cl. .................... 428/402.21; 264/4.1; 264/4.3; 264/4.33; 427/213.3; 427/213.36; 428/402.2; 428/403
(58) Field of Search ................. 264/4.1, 4.3, 4.33; 427/213.3, 213.36; 428/402.2, 402.21, 403

(56) References Cited

U.S. PATENT DOCUMENTS

| | | |
|---|---|---|
| 3,523,906 A | 8/1970 | Vrancken et al. |
| 4,389,330 A | 6/1983 | Tice et al. |
| 5,004,602 A | 4/1991 | Hutchinson |
| 5,019,400 A | 5/1991 | Gombotz et al. |
| 5,100,669 A | 3/1992 | Hyon et al. |
| 5,320,840 A | 6/1994 | Camble et al. |
| 5,942,253 A | 8/1999 | Gombotz et al. |
| 6,020,004 A | 2/2000 | Shah |

FOREIGN PATENT DOCUMENTS

| | | |
|---|---|---|
| JP | 2001-190943 A | 7/2001 |
| WO | WO 01/15799 A1 | 3/2001 |

OTHER PUBLICATIONS

R. Arshady, "Microspheres, Microcapsules, and Liposomes: General Concepts and Critera" MML Series, 1999, pp. 11–45, vol. 1, Citus Books, London.

C. Thies, "A Survey of Microencapsulation Processes," Microencapsulation: Methods and Industrial Applications. 1996, pp. 1–19, Marcel Dekker, New York.

J. Benoit, et al. "Biodegradable Microspheres: Advances in Production Technology", Microencapsulation: Methods and Industrial Applications. 1996, pp. 35–72, Marcel Dekker, New York.

(List continued on next page.)

Primary Examiner—Samuel A. Acquah
(74) Attorney, Agent, or Firm—Medicus Associates; James H. Meadows

(57) ABSTRACT

A solvent exchange method is employed to provide microencapsulated compositions, such as microcapsules of pharmaceutical preparations. The method is based on an exchange of water and a hydrophilic organic solvent, whereby a decline in solvent quality for the organic solvent causes a polymer dissolved therein to be deposited onto an aqueous core. Optimal results are rationalized in terms of a balance of water solubility and surface tension for the organic solvent. In a preferred embodiment, microcapsules of selected drugs are formed by contacting microdroplets of an aqueous solution containing the drug with the organic solvent containing a polymer dissolved therein. A preferred method employs biodegradable poly(lactic acid-co-glycolic acid) (PLGA) dissolved in acetic acid, ethyl acetate, methyl acetate, or ethyl formate, to form a PLGA membrane around an aqueous drug core. The method is particularly attractive for encapsulating protein-based drugs without substantial denaturation.

16 Claims, 4 Drawing Sheets

OTHER PUBLICATIONS

E. Allemann, et al. "Drug–loaded Nanoparticles—Preparation Methods and Drug Targeting Issues," *Eur. J. Pharm. Biopharm.*, 39: 173–191, 1993.

H. Okada et al. "Biodegradable Microspheres in Drug Delivery," *Critical Rev. in Therapeutic Drug Carrier Systems* 12(1): 1–99, 1995.

J. Li, et al., "A novel biodegradable system based on gelatin nanoparticles and poly(lactic–co–glycolic acid) microspheres for protein and peptide drug delivery," *J. Pharm. Sci.* 86(8): 891–895, 1997.

N. Wang et al. "A novel approach to stabilization of protein drugs in poly(lactic–co–glycolic acid) microspheres using agarose hydrogel," *Int. J. Pharm.* 166: 1–14, 1998, Elsevier.

S. Schwendeman, et al. "New strategies for the microencapsulation of tetanus vaccine," *J. Microencapsulation* 15: 299–318, 1998.

S. Zhou et al. "Investigation on a novel core–coated microspheres protein delivery system," *J. Controlled Release*, 75: 27–36, 2001.

K. Park, et al. "Biodegradable Hydrogels for Drug Delivery," 1993, pp. 99–140, Technomic Publishing Co., Inc. Lancaster, PA.

M. Weert et al. "Protein instability in poly(lactic–co–glycolic acid) micro–particles," *Pharm Res.* 17(10): 1159–1167, 2000.

H. Le "Progress and trends in ink–jet printing techonlogy," *J. Imaging Sci. Technol.,* 42: 49–62, 1998.

M. Mumenthaler, et al. "Feasibilty study on spray–drying protein pharmaceuticals: Recombinant human growth hormone and tissue–type plasminogen activator," *Pharm. Res.* 11: 12–20, 1994.

Y. Maa, et al. "Spray–drying of air–liquid interface sensitive recombinant human growth hormone," *J. Pharm. Sci.* 87: 152–159, 1998.

B. Knutson, et al. "Preparaton of microparticulates using supercritical fluids," Microparticulate Systems for the Delivery of Proteins and Vaccines. 1996, pp. 89–125, Marcel Dekker, Inc., New York, NY.

R. Ghaderi, et al. "Preparation of biodegradable microparticles using solution–enhanced dispersion by supercritical fluids (SEDS)," *Pharm. Res.* 16:676–681, 1999.

O. Johnson, et al. "Peptide and protein drug delivery," Encyclopedia of Controlled Drug Delivery. Mathiowitz, E., Ed., 1999, 816–833, John Wiley & Sons, Inc., New York, NY.

H. Sah, "Protein instability toward organic solvent/water emulsification: Implications for protein microencapsulation into microspheres," *PDA J. Pharm. Sci. & Technol.* 53:3–10, 1999.

M. Morlock, et al. "Microencapsulation of rh–erythropoietin, using biodegradable poly(D,L–lactide–co–glycolide): protein stability and the effects of stabilizing excipients," *Eur. J. Pharm. Biopharm.* 43: 29–36, 1997.

D. Peregrine, et al. "The bifurcation of liquid bridges," *J. Fluid Mech.,* 212: 25–39, 1990.

X. Zhang, et al. "An experimental study of dynamics of drop formation," *Phys. Fluids*, 7: 1184–1203, 1995.

E. Wilkes, et al. "Computational and experimental analysis of dynamics of drop formation," *Phys. Fluids*, 11: 3577–3598, 1999.

M. Blanco–Prieto, et al. "In vitro and in vivo evaluation of a somatostatin analogue released from PLGA microspheres," *J. Controlled Rel* 67: 19–28, 2000.

R. Eliaz, et al. "Characterization of a polymeric PLGA–injectable implant delivery system for the controlled release or proteins," *J. Biomed. Mater. Res.* 50: 388–396, 2000, John Wiley & Sons, Inc.

W. Lambert, et al. "Development of an in situ forming biodegradable polylactide–co–glycolide system for the controlled release of proteins," *J. Controlled Rel.* 33: 189–95, 1995.

H. Ravivarapu, et al. "Sustained suppression of pituitary––gonadal axis with an injectable, in situ forming implant of leuprolide acetate," *J. Pharm. Sci.* 89: 732–741, 2000.

R. Jain, et al. "Controlled delivery of drugs from a novel injectable in situ formed biodegradable PLGA microsphere system," *J. Microencaps.* 17: 343–362, 2000.

R. Bodmeier, et al. "Solvent selection in the preparation of poly(DL–lactide) microspheres prepared by the solvent evaporation method," *Int. J. Pharm.,* 43: 179–186, 1988.

C. Berkland, et al. "Fabrication of PLG microspheres with precisely controlled and monodisperse size distributions," *J. Controlled Rel.* 73: 59–74, 2001.

S. Lahooti, et al. "26. Methods for microencapsulation with HEMA–MMA," Methods in Molecular Medicine. 1999, 331–348, vol. 18, Humana Press Inc., Totowa, NJ.

C. Hansen "The three dimensional solubility parameter—key to paint component affinities: II and III," *J. Paint Technology* 39(511): 505–514, 1967.

J. Teas, "Graphic analysis of resin solubilities," *J. Paint Technology* 40(516): 19–25, 1968.

A. Barton, "Solubility parameters," *Chemical Reviews* 75(6): 731–753, 1975.

MICROENCAPSULATION OF DRUGS BY SOLVENT EXCHANGE

REFERENCE TO RELATED APPLICATIONS

The present application is related to U.S. provisional patent application No. 60/254,920, filed Dec. 13, 2000, and No. 60/294,263, filed May 31, 2001.

FIELD OF THE INVENTION

The present invention relates to pharmaceutical compositions and methods of drug delivery. The invention especially relates to methods and compositions for providing controlled release of proteinaceous drugs.

BACKGROUND OF THE INVENTION

Controlled drug delivery technologies have advanced significantly over the last few decades and current technologies afford delivery of drugs at predetermined rates for days and years depending on the application. These advances, however, are applicable mostly to low molecular weight drugs. It is still difficult to develop controlled release formulations for long-term delivery of high molecular weight drugs, such as peptides, proteins, oligonucleotides, and genes. The delivery of high molecular weight drugs has become especially significant since the development of recombinant DNA technology, which has made possible large-scale production of such protein drugs as tissue plasminogen activator (TPA), erythropoietin (EPO), interferon, insulin, and a number of growth factors. Furthermore, completion of the genome project is expected to result in an improved understanding of the therapeutic roles of many different proteins, which should lead to numerous new protein drugs.

Almost all protein drugs are short acting, requiring repeated injections to maintain therapeutic efficacy. Many drugs, such as human growth hormone, luteinizing hormone-releasing hormone, interferons, cyclosporins, and TPA, are therapeutically useful only by following a therapeutic regimen that may require multiple injections daily. This means that therapeutic applications and commercialization of these drugs rely heavily on the successful development of viable delivery systems, which can improve their biochemical and biophysical stability and systemic bioavailability. Development of nonparenteral routes of administration, such as oral, nasal, pulmonary, ocular, buccal, vaginal, rectal, and transdermal routes, are highly desirable, but to date delivery through such routes is very difficult, if not impossible. The high molecular weights and enzymatic degradations of protein drugs make them particularly difficult to deliver non-parenterally.

Currently, the main goal in delivery of protein-based pharmaceuticals is to develop controlled release formulations that permit long-term delivery ranging from weeks to months from a single administration. For such applications, biodegradable polymers are very attractive, especially when their degradation products are known to be innocuous or biocompatible. They need not be surgically removed at the end of a treatment. Commonly used biodegradable polymers, which have been investigated for the controlled delivery of protein drugs, include homopolymers of poly (lactic acid) (PLA) or poly(glycolic acid) (PGA), poly(lactic acid-co-glycolic acid) (PLGA), poly(ortho esters), and polyanhydrides. Of these, PLGA has been used most frequently. Due to the long history of clinical applications of PLGA, it has become a polymer of choice for developing most protein drug delivery systems. A number of excellent reviews discuss currently available microencapsulation methods (1,2).

In discussing different approaches of microencapsulation, it is useful to understand the terminologies commonly used in the microencapsulation field. The process of microencapsulation results in "microparticles." Microparticles can be divided into "microspheres" and "microcapsules," which are different from each other. Microspheres usually refer to a monolithic type formulation in which the drug molecules are dispersed throughout the polymeric matrix (1, 2). On the other hand, microcapsules refer to reservoir devices in which the drug core is surrounded by a continuous polymeric layer or membrane. The drug core can be single (mononuclear) or multiple (multinuclear) inside the polymer membrane (3–5), but mononuclear microcapsules are generally preferred for drug delivery.

There are a number of advantages of microcapsules over microspheres. First of all, microcapsule formulations provide much more drug reservoir space than microspheres. In microcapsules only a minimal amount of the drug compound is in contact with organic solvent during processing and with the polymer coating after the microcapsules are formed. In contrast, protein drugs in microspheres are dispersed throughout the polymer matrix, but the large contact areas between protein drugs and solid polymer component may be unfavorable for protein stability. In microcapsules, protein drugs can be further protected from degrading polymers using another layer of a hydrophilic material or matrix before microencapsulation. For example, drug-containing nanoparticles made of gelatin, agarose, or poly(vinyl alcohol) suspended in an organic solvent containing a dissolved polymer (e.g., PLGA in methylene chloride) form multinuclear microcapsules by phase separation methods (6, 7) or by solvent extraction methods (8, 9). Microcapsules also provide desirable zero-order release as compared to the ever-decreasing release rate obtained by microspheres.

The current methods used for the preparation of microencapsulated pharmaceutical products are listed below, each of which has its own advantages, limitations and drawbacks. While the methods listed have been used to produce successful commercial products, many protein drugs cannot be formulated using such methods. Considering that a large number of protein drugs are available now and will be produced in the near future, it is clear that new, improved protein delivery systems need to be developed.

Solvent evaporation and solvent extraction
    Coacervation (Simple and complex coacervation)
    Hot melt microencapsulation (congealing)
    Interfacial cross-linking and interfacial polymerization
    Spray drying
    Supercritical fluid
    Solvent evaporation and solvent extraction methods utilize volatile organic solvents for dissolving water-insoluble polymers, such as PLGA. Commonly used organic solvents are methylene chloride, ethyl acetate, and methyl ethyl ketone. A double emulsion process is commonly used for producing PLGA microspheres containing water-soluble drugs, including protein drugs. Both solid/oil/water (s/o/w) and water/oil/water (w/o/w) systems are used depending on the type of drug (10). A drug in soluble or dispersed form is added to the polymer solution, and the mixture is then emulsified in an aqueous phase containing a surface-active agent, such as poly(vinyl alcohol). In the solvent evaporation method, the organic solvent is evaporated by raising the temperature and/or by applying vacuum. See, for example, U.S. Pat. No. 3,523,906 (issued to Vrancken, et al.). In the solvent extraction method, the organic solvent diffuses into the water phase to make emulsion droplets into solid polymer microspheres. See, for example, U.S. Pat. No. 4,389,330 (issued to Tice, et al.). In both methods, the continuous phase can be non-miscible oils. The organic solvent conventionally employed in this method is a chlorinated hydrocarbon, such as methylene chloride, of which a residual amount is strictly controlled under 600 ppm for the known toxicities. In addition, the loading capacity of microspheres prepared by the solvent extraction and solvent evaporation is in general low. Furthermore, the way emulsions are created increases not only the total interfacial area the bioactive materials are subjected to, but also the extent of shear and cavitation stress which may be destructive to bioactive materials (12).

To minimize the loss of activity of the bioactive materials, it has been proposed to make microspheres at very low temperatures. See, e.g., U.S. Pat. No. 5,019,400 (issued to Gombotz, et al.). Biodegradable polymer is dissolved in an organic solvent, such as methylene chloride, together with protein powders, and then atomized over a bed of frozen ethanol overlaid with liquid nitrogen. The microdroplets freeze upon contacting the liquid nitrogen, and then sink onto the frozen ethanol layer. As the ethanol layer thaws, the frozen microspheres sink into the ethanol. Methylene chloride, the solvent in the microspheres, then thaws and is slowly extracted into the ethanol, resulting in hardened microspheres containing proteins and a polymer matrix. This process, which utilizes liquid nitrogen and methylene chloride, is not easy, especially for scale-up mass production.

The coacervation method is based on salting out (or phase separation) from a homogeneous polymer solution of hydrophilic polymers into (small droplets of) a polymer-rich, second liquid phase, rather than into solid aggregates. When an aqueous polymer solution (e.g., gelatin or carboxymethylcellulose) is partially dehydrated (or desolvated) by adding a strongly hydrophilic substance (e.g., sodium sulfate) or a water-miscible, non-solvent (e.g., ethanol, acetone, dioxane, isopropanol, or propanol), the water-soluble polymer is concentrated in water to form the polymer-rich phase. This is known as "simple" coacervation. If water-insoluble drug particles are present as a suspension or as an emulsion, the polymer-rich phase is formed on the drug particle surface to form a capsule under suitable conditions. In "complex" coacervation, the polymer-rich complex (coacervate) phase is induced by interaction between two dispersed hydrophilic polymers (colloids) of opposite electric charges. Since electrostatic interactions are involved, the pH of the medium is very important to control the charges of the polymers.

In hot melt microencapsulation (also called congealing), a solid drug or liquid drug is mixed with the polymer melted at high temperatures. The mixture is then suspended in a non-miscible solvent with continuous stirring at a temperature several degrees above the melting point of the polymer. After the emulsion is stabilized, the system is cooled until the polymer particles solidify. The drug has to be stable at the polymer melting temperature. For interfacial cross-linking, the polymer must possess functional groups that can be cross-linked by ions or multi-functional molecules. Interfacial polymerization requires monomers that can be polymerized at the interface of two immiscible substances to form a membrane, and thus removal of the unreacted monomers from the final product becomes an issue.

For spray drying, a drug is dissolved or suspended in a suitable (either aqueous or non-aqueous) solvent that contains dissolved polymer materials. The drug can be dissolved or suspended in the solvent. Alternatively, the drug solution can be emulsified in the polymer solution. The solution is atomized and microspheres are dried by a heated carrier gas. The temperature of inlet gas can be 90–150° C. for protein drugs (14, 15). The microsphere size is controlled by the rate of spraying, the feed rate of the drug-polymer solution, the nozzle size, and temperature in the drying and cooling chambers. This seemingly simple process has not been used widely in the pharmaceutical industry due, in part, to the difficulties in the scale-up process. The parameters optimized in the laboratory scale spray drier do not usually work for the much larger industrial scale spray drier. Spray drying and hot melt microencapsulation methods have not been used as frequently as the solvent evaporation and solvent extraction methods due to the need for high temperature, which can easily denature protein drugs.

A supercritical fluid is defined as a fluid for which the temperature and pressure are simultaneously higher than those at the critical point (i.e., critical temperature $T_c$ and critical pressure $P_c$), at which the density of gas is equal to that of the remaining liquid and the surface between the two phases disappears. Microparticles have been prepared by either rapid expansion of supercritical solutions (RESS) or supercritical antisolvent crystallization (SAS) (16). RESS exploits the liquid-like solvent power of the supercritical fluids whereas SAS uses supercritical fluid as an antisolvent. Carbon dioxide is most commonly used for the critical conditions are easily attainable, i.e., $T_c=31°$ C. and $P_c=73.8$ bar. It is also environmentally benign, relatively non-toxic, non-inflammable, inexpensive, and has a reasonably high dissolving power (17). RESS is limited by the constraint that all solutes should be soluble in the supercritical fluid. For this reason, RESS may not be used for protein encapsulation using polymers, because of their low solubility in common supercritical fluids. SAS is suitable for processing of solids difficult to solubilize in supercritical fluids, such as peptides and proteins. The supercritical fluid approach does not provide any significant advantages over the other methods listed above. Furthermore, the supercritical fluid approach produces only microspheres and the production of microcapsules is extremely difficult.

Protein drugs for long-term application have been most frequently formulated into microspheres made of biodegradable poly(lactic-co-glycolic acid) (PLGA). PLGA is the polymer of choice, since it has been used for a variety of clinical applications and is known to be biocompatible. For this reason, there has been little reason to use other polymers, unless use of PLGA is impossible.

Of the microencapsulation methods listed above, solvent evaporation and solvent extraction methods have been most frequently employed with PLGA, since it is not water-soluble (18). The solvent evaporation and extraction methods have had limited success with a few select therapeutic proteins (19–20). Also, see U.S. Pat. No. 5,942,253 (issued to Gombotz, et al.) and U.S. Pat. No. 6,020,004 (issued to Shah). These methods, however, are not suitable for the majority of proteins due to lengthy procedures and difficulty in scale up for mass production. In many cases, contacts between protein and solvent throughout the microsphere matrix may cause denaturation of most protein drugs to be loaded. Because of the problems associated with using organic solvents, the solvent evaporation and extraction methods have not been used as a universal method for making microparticles of protein drugs. To avoid the use of chlorinated organic solvents in microsphere formation, methylene chloride has been replaced with less toxic solvents, such as ethyl acetate, N-methylpyrrolidone, methyl ethyl ketone or acetic acid. PLGA polymer is then precipitated by adding alcohol as a non-solvent and water as a hardening agent (PCT Publication WO 01/15,799 of Benoit, et al.). In this phase separation approach, which is similar to coacervation discussed above, protein drugs have to be exposed to organic solvents for a prolonged period of time, and the prepared microspheres are prone to aggregation. In addition, the use of water as a hardening agent may not be ideal for water-soluble drugs, including protein drugs that can dissolve and leach out from the microspheres into the water phase. Since protein drugs will be directly in contact with the polymer matrix, protein molecules may adsorb to the solid surface and become denatured.

Some patent references propose use of acetic acid in the preparation of microspheres such as those made from PLGA. U.S. Pat. No. 5,100,669 (issued to Hyon et al.) propose use of glacial acetic acid to prepare a solution containing both PLGA and an active substance, such as leutenizing hormone releasing hormone (LHRH). PLGA-dissolved glacial acetic acid was mixed with 1/10 volume of aqueous solution of LHRH to obtain complete dissolution of the polymer and the active substance. This solution was added dropwise to oil to prepare an emulsion. Microspheres were obtained by removing water and acetic acid by solvent evaporation at elevated temperatures. The process was used to dissolve both PLGA and an active substance in the same solvent, e.g., acetic acid-water mixture.

U.S. Pat. No. 5,004,602 (issued to Hutchinson) and U.S. Pat. No. 5,320,840 (issued to Camble et al.) propose use of acetic acid to dissolve both PLGA and protein drugs in the same solvent. Glacial acetic acid with dissolved PLGA and protein drug were freeze dried to obtain a powder form that can be pressed at elevated temperatures. The acetic acid solution containing both PLGA and peptide drug (e.g., somatostatin analogue) was spray dried to obtain microspheres (27). In another application, PLGA was dissolved in glacial acetic acid and subsequently freeze-dried to make PLGA foams for sustained drug delivery. Clearly, acetic acid was used in the literature mainly for the purpose of dissolving PLGA and active agents in the same solvent. Protein drugs may be dispersed in the same solvents and microspheres may be made using conventional solvent extraction and evaporation methods utilizing s/o/w or w/o/w emulsions or using the spray drying method.

It is desired to develop a method of forming microencapsulated drugs, e.g., as microspheres or microcapsules, in which the drug remains substantially stable and is not denatured or inactivated by the manufacturing process. Organic solvents used in the method should not have excessive toxicities so that any incorporation into the pharmaceutical preparation does not present deleterious side effects. Especially desired are novel formulations and manufacturing methods of protein drugs, which maintain their efficacy and permit sustained and/or controlled release over extended periods.

SUMMARY OF THE INVENTION

The present invention is for an encapsulated composition and method for making the same. An encapsulated composition can be any encapsulated entity, such as those encountered in the pharmaceutical, paint, and adhesive industries. Preferably, and most generally, the encapsulated composition contains a physiologically active substance as the core material and exhibits controlled release properties. More preferably, the physiologically active substance is a protein.

A manufacturing method of the present invention comprises: (i) providing an aqueous solution composed of water and a core substance dissolved therein; (ii) providing a polymer solution composed of a water-miscible or soluble solvent and a water-insoluble polymer dissolved therein; (iii) forming a droplet of the aqueous solution containing the core substance; and (iv) admixing the droplet of aqueous solution with at least a portion of the polymer solution under conditions permitting the water-insoluble polymer to deposit on the core substance to afford the encapsulated composition. Preferably, the core substance is a protein drug and the water-insoluble polymer is biocompatible. More preferably the polymer is biodegradable, such as poly(lactic acid-co-glycolic acid) (PLGA). Particularly preferred water-miscible or soluble solvents include acetic acid, methyl acetate, ethyl acetate, and ethyl formate.

In a preferred embodiment of the invention, microdroplets of an aqueous drug (e.g., a protein) solution are contacted with microdroplets of a hydrophilic organic solvent having a polymer dissolved therein. At the interface of water and solvent, solvent exchange occurs resulting in a lowering of solvent quality for the dissolved polymer. The polymer thereby precipitates onto the surface of the aqueous microdroplets to form a membrane therearound. The desired interface between water and organic solvent can be created by many techniques, some of which were described in the examples hereinafter.

The exchange between water and organic solvent at the droplet interface is a key aspect of the present invention, thus this process is called a "solvent exchange method." Only a minute fraction of protein drugs are directly exposed to the polymer solvent by this method, thereby minimizing the potential for protein denaturation. The solvent exchange method can also permit easy scale-up for mass production.

The present invention may be further understood with reference to the attached drawings, which illustrate non-limiting embodiments of the present invention.

DESCRIPTION OF THE INVENTION

Figure 1:
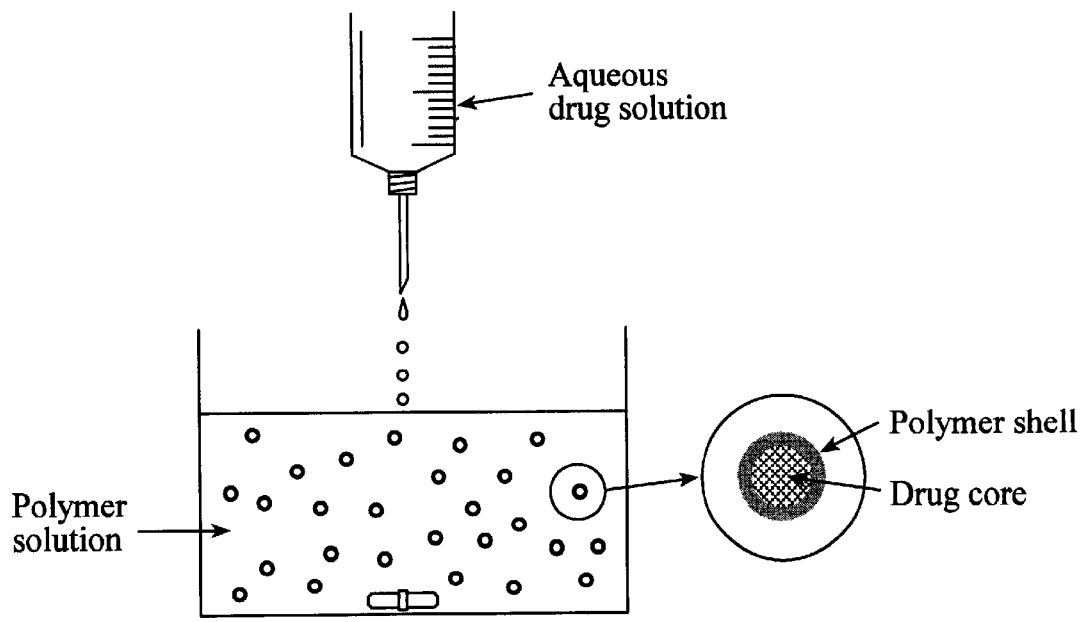
FIG. 1 depicts dropwise addition from a syringe/needle of an aqueous drug solution into a solution of polymer to form microspheres or microcapsules having a polymer shell around a drug core. The polymer, e.g., PLGA, deposits onto the drug core immediately upon contact due to fast dilution of polymer solvent, e.g., acetic acid, in the proximity of the aqueous droplets.

The present invention provides encapsulated compositions and methods of making the same. The invention employs solvent exchange to produce microparticles, preferably microcapsules, in which a single hydrophilic core is surrounded by a polymer coat. The principle of solvent exchange method of the present invention is that a suitable polymer can be dissolved in a hydrophilic organic solvent, but it becomes phase separated upon only a small decrease in the solvent quality, i.e., reduced mole fraction of the solvent. The hydrophilic solvent mixes with water at the interface between an aqueous core and the polymer solution. This solvent exchange on the surface of the aqueous core brings about a slight decrease of polymer solubility and results in deposition of a polymer coat around the hydrophilic core. Microcapsules so formed can be collected and further hardened in a water bath, e.g., one containing a surfactant to prevent aggregation of microcapsules.

A typical microcapsule has a size dimension less than about 1 mm in size, more generally in the range of about 0.5 micron to about 1000 microns. The aqueous core of a microcapsule has a dimension in the range of about 0.1 micron to about 600 microns, more preferably about 1 to about 50 microns. The outer polymer layer typically has a thickness in the range of about 0.1 micron to about 300 microns.

An important aspect of one embodiment of the invention is the use of one or more hydrophilic organic solvents miscible or soluble in water, which can serve as a solvent for a biodegradable polymer. Examples of such hydrophilic organic solvents include acetic acid, ethyl acetate, glycofurol (28), N-methylpyrrolidone (29, 30), triacetin (31), dimethyl sulfoxide (29), methyl ethyl ketone, and benzyl alcohol, most of which have been used previously in injectable drug delivery systems. The literature relates only limited use of hydrophilic organic solvents in the preparation of microspheres.

A biodegradable biocompatible polymer of the present invention can serve as the encapsulating material, which deposits on the aqueous core. The polymer is preferably selected from among poly(lactides), poly(glycolides), poly(lactide-co-glycolides), polycaprolactone, polycarbonates, polyesteramides, polyanhydrides, poly(amino acids), polyorthoesters, poly(dioxanones), poly(alkylene alkylate)s, polyacetals, polycyanoacrylates, biodegradable polyurethanes, blends and copolymers thereof. Polymers comprising poly(lactides), copolymers of lactides and glycolides, blends thereof, or mixtures thereof are preferred. Such polymers can be formed from monomers of a single isomeric type or a mixture of isomers. A non-biodegradable, biocompatible polymer can also be used in the present invention and is preferably selected from polyacrylates, polymers of ethylene-vinyl acetates and other acyl substituted cellulose acetates, non-degradable polyurethanes, polystyrenes, polyvinyl chloride, polyvinyl fluoride, poly(vinyl imidazole), chlorosulphonate polyolefins, polyethylene oxide, blends and copolymers thereof.

In one approach, PLGA is dissolved in a hydrophilic organic solvent and to this solution are added microdroplets of aqueous protein solution. As used herein, a "microdroplet" refers to a drop size typically in the range from about 0.1 micron to about 1000 microns. Upon interaction between the water in the aqueous protein droplets and the organic solvent (e.g., acetic acid), exchange of both liquids occurs at the droplet surface to deposit PLGA on the protein core, e.g., as a thin membrane.

In another approach, a microdroplet of aqueous protein solution is generated by a "microdispenser", which as used herein refers to at least one nozzle, e.g., of the ink jet type. As used herein, a microdispenser is a dispensing device capable of generating a microdroplet, e.g., by having a sufficiently small orifice size. The microdroplet interacts with another microdroplet of PLGA-dissolved hydrophilic organic solvent. Due to the differences in surface tension, the PLGA/organic solvent spreads over the aqueous microdroplet to coat it with a PLGA layer. Numerous microdroplets can be generated using microdispensers, e.g., with a plurality of nozzles, and the formed PLGA-coated aqueous microdroplets are then collected in aqueous solution. Solvent exchange occurs at the interface between aqueous microdroplet and PLGA/organic solvent, and also at the interface between PLGA/organic solvent and aqueous solution. This process leads to formation of a PLGA shell on the surface of aqueous protein microdroplets.

A number of variations on the microencapsulation method are possible. To the aqueous protein solution can be added other polymers that undergo sol-gel phase transition for the purpose of making the protein core stronger and/or controlling the drug release rate. Examples are sodium alginate (that can become a gel upon contact with calcium ions in the PLGA/solvent), chitosan (forming a gel with multivalent anions or anionic polymers) (10), and other thermosensitive gelling systems. The protein drug cores can also be covered with a protecting layer to keep the protein drugs isolated to prevent denaturation. Because of its simplicity and minimal exposure of protein drugs to denaturating conditions, the solvent exchange method can be used for a variety of proteinaceous drugs, such as antibodies, enzymes, ligands, hormones, cytokines, and the like. Examples include erythropoietin, growth hormone, insulin, interferon, interleukins, G-CSF, epidermal growth factors, tumor necrosis factor, and other protein pharmaceuticals yet to be developed.

Formation of a polymer layer on the surface of a hydrophilic core (i.e., aqueous droplet or hydrogel) depends on the choice of organic solvents used to dissolve the polymer. The two most important parameters in the selection of suitable solvents for the solvent exchange method are water solubility and surface tension. The water solubility of the solvent determines how easily solvent exchange occurs, and thus, how fast the polymer phase separation occurs to form a polymer membrane (or a layer) at the solvent-water interface. Once the solvent has proper water solubility, the surface tension of the solvent determines whether the solvent can cover the aqueous droplets easily. In making the microcapsules, biocompatibility of the solvents used may not be the critical factor, since the residual solvent in the final microcapsules will be much lower than the limit allowed for human applications. However, use of biocompatible solvents, if available, is preferred over other toxic solvents. Preferred solvents are those used in drug formulations approved by the FDA for clinical applications. Suitable solvents for solvent exchange methods are those with Hildebrand solubility parameters in the range of about 16 to 24 MPa$^{1/2}$, preferably about 18 to 23 MPa$^{1/2}$. (The solubility parameter is defined as the square root of the cohesive energy density.) Suitable solvents also are freely water-miscible or water-soluble, i.e., greater than about 5% w/v, preferably 5 to 50% w/v). The surface tension for the solvent is preferably less than about 45 mN/m, more preferably less than about 30 mM/m. Selection of the optimum solvent for a given solvent exchange method depends on the nature of the polymer used for making microcapsules.

A nonexclusive list of solvents that can be used for the solvent exchange method includes: acetic acid, acetone, acetonitrile, acetyl acetone, acrolein, acrylonitrile, allyl alcohol, 1,3-butanediol, 1,4-butanediol, 1-butanol, 2-butanol, tert-butanol, 2-butoxyethanol, n-butyl amine, butyl dioxitol acetate, butyraldehyde, butyric acid, 2-chloroethanol, diacetone alcohol, diacetyl, diethylamine, diethylene glycol diethyl ether, diethylene glycol dimethyl ether, diethylene glycol monobutyl ether, diethylene glycol monobutyl ether acetate, diethylene glycol monoethyl ether, diethylene glycol monoethyl ether acetate, diethylene glycol monomethyl ether, N,N-diethylnicotinamide, dimethyl sulfoxide, N,N-dimethylacetamide, N,N-dimethylformamide, 1,4-dioxane, 2-ethoxyethanol, 2-ethoxyethyl acetate, ethyl acetate, ethyl formate, ethylene glycol methyl ether acetate, formic acid, furfural, glycofurol, hexylene glycol, isobutanol, isopropyl alcohol, 2,6-lutidine, methyl acetate, methyl ethyl ketone, methyl isopropyl ketone, methyl propionate, N-methylpyrrolidone, morpholine, tert-pentanol, 2-picoline, 3-picoline, 4-picoline, piperidine, 1-propanol, propionaldehyde, propylene oxide, pyridine, pyrimidine, pyrrolidine, tetrahydrofuran, tetramethylurea, triacetin, triethylene glycol, trimethyl phosphate. Although preferred solvents for use in the solvent exchange method are those having water solubility of 5% or higher, solvents of lower water solubility (<5%) can also be used to make microcapsules in a similar manner.

When the water solubility of the solvent is low, the formation of polymer membrane is rather governed by solvent extraction to a larger quantity of aqueous solution than by rapid solvent exchange on the surface of the aqueous core. In this case, solvent exchange is too slow to be dominant for microcapsule formation. The same mechanism can be employed regardless of the water solubility of solvents and the principle of membrane formation in making mononuclear microcapsules. Examples of solvents having low water solubility (<5%) but which may be used include acetic acid isopropyl ester (isopropyl acetate), acetic acid sec-butyl ester, acetophenone, n-amyl acetate, aniline, benzaldehyde, benzene, benzophenone, benzyl alcohol, benzyl amine, benzyl benzoate, bromobenzene, bromoform, n-butyl acetate, butyric acid methyl ester, caproic acid, carbon disulfide, carbon tetrachloride, o-chloroaniline, chlorobenzene, 1-chlorobutane, chloroform, chloromethane, m-chlorophenol, m-cresol, o-cresol, cyanoethane, cyanopropane, cyclohexanol, cyclohexanone, 1,2-dibromoethane, dibromomethane, dibutyl amine, m-dichlorobenzene, o-dichlorobenzene, 1,1-dichloroethane, 1,2-dichloroethane, dichlorofluoromethane, diethyl carbonate, diethyl malonate, diethyl sulfide, diethylene glycol dibutyl ether, diisobutyl ketone, diisopropyl sulfide, dimethyl phthalate, dimethyl sulfate, dimethyl sulfide, N,N-dimethylaniline, enanthic acid, ethyl acetoacetate, ethyl benzoate, ethyl propionate, ethylbenzene, ethylene glycol monobutyl ether acetate, exxate 600, exxate 800, exxate 900, fluorobenzene, furan, hexamethylphosphoramide, 1-hexanol, n-hexyl acetate, isoamyl alcohol (3-methyl-1-butanol), isobutyl acetate, methoxybenzene, methyl amyl ketone, methyl benzoate, methyl formate, methyl isoamyl ketone, methyl isobutenyl ketone, methyl isobutyl ketone, methyl n-butyl ketone, methyl propyl ketone, 4-methyl-2-pentanol, N-methylaniline, methylene chloride, nitrobenzene, nitroethane, 1-nitropropane, 2-nitropropane, 1-octanol, 2-octanol, 1-pentanol, 3-pentanone, 2-phenylethanol, n-propyl acetate, quinoline, styrene, 1,1,2,2-tetrachloroethane, 1,1,2,2-tetrachloroethylene, toluene, 1,1,1-trichloroethane, 1,1,2-trichloroethane, 1,1,2-trichloroethylene, trifluoromethane, valeric acid, m-xylene, o-xylene, p-xylene, 2,4-xylenol.

Two or more different solvents can be used as admixtures to control the kinetics of phase separation during the microencapsulation process. Those solvents of low water solubility can also be used as a component of the mixture with the preferred hydrophilic solvents. For example, chloroform is not highly water miscible with the 0.8% solubility in water. Thus, chloroform in itself is not a preferred solvent for the solvent exchange method; however, it can be used as an admixture with a hydrophilic solvent to provide a control over the kinetics and the extent of polymer phase separation, i.e., precipitation. By mixing relatively hydrophobic solvents and hydrophilic solvents at various ratios, the kinetics and extent of polymer phase separation can be controlled for optimization of the thickness and surface smoothness of the formed microcapsules. The use of solvent mixture is also beneficial since it may allow much more flexible selection of solvents considering the degree of toxicity or environmental effects.

The data in Table 1 illustrates the importance of the water solubility and surface tension of solvent in making polymer capsules on aqueous droplets using PLGA as a model polymer. A selected number of solvents with varying water solubility and surface tension were chosen and tested for their ability to make polymer membrane around aqueous droplets. Table 1 lists various solvents and the results obtained with some of them. In this particular example, two methods were used for testing. In one method, each microdroplet of aqueous solution was collided with another microdroplet of organic solvent to examine whether the water solubility and surface tension influence the microcapsule formation as predicted by theory. In another method, aqueous droplets were introduced into the polymer-dissolved solvent and the formation of polymer capsule was examined.

TABLE 1

Effect of water solubility and surface tension on the formation of microcapsule around microdroplet. (Only good solvents for PLGA were tested.)

| Solvent | Water Solubility (%) | Surface Tension (mN/m) | Microcapsule Formation |
|---|---|---|---|
| Propylene oxide | 59 | 22.2 | |
| Acetone | >100 | 22.68 | White precipitate |
| n-butyl amine | >100 | 23.17 | |
| Tetrahydrofuran | >100 | 26.4 | White precipitate |
| Diethylene glycol diethyl ether | >100 | 26.68 | White precipitation |
| Butyric acid | >100 | 26.8 | |
| 2-butoxyethanol | >100 | 27.4 | |
| Ethylene glycol methyl ether acetate | >100 | 27.4 | |
| Acetic acid | >100 | 27.42 | Yes, White membrane |
| 2-ethoxyethanol | >100 | 28.2 | |
| Diethylene glycol monomethyl ether | >100 | 28.49 | |
| Diethylene glycol dimethyl ether | >100 | 29.5 | |
| Diethylene glycol monoethyl ether | >100 | 29.53 | |
| Diacetone alcohol | >100 | 31 | |
| Diethylene glycol monoethyl ether acetate | >100 | 31.4 | |
| N,N-Dimethylacetamide | >100 | 32.43 | White precipitate |
| 1,4-Dioxane | >100 | 32.8 | |
| Hexylene glycol | >100 | 33.1 | |
| Formic acid | >100 | 37.58 | |
| N-methylpyrrolidone | >100 | 40.7 | White precipitate |
| Dimethyl sulfoxide | >100 | 42.98 | White precipitate |
| Triethylene glycol | >100 | 45.2 | |
| Acrolein | 21.25 | 23.14 | |
| Ethyl acetate | 8 | 23.75 | Yes |
| Ethyl formate | 10.5 | 24 | Yes |
| Methyl acetate | 24.4 | 24.1 | Yes |
| Methyl ethyl ketone | 22.3 | 24.6 | |
| Methyl isopropyl ketone | 6 | 24.61 | |
| Acrylonitrile | 7 | 27.3 | |
| Butyraldehyde | 7 | 30 | |
| Diethylene glycol monobutyl ether acetate | 6.5 | 30 | |
| Acetyl acetone | 16 | 31.2 | |
| 2-ethoxyethyl acetate | 23 | 31.8 | |
| Butyl dioxitol acetate | 6.5 | 32.2 | |
| Furfural | 7.9 | 41.1 | |
| Acetic acid, isopropyl ester | 3.09 | 22.1 | |
| Methyl formate | 3 | 25 | |
| Chloroform | 0.8 | 26.5 | Yes |
| Methylene chloride | 1.3 | 27.89 | Yes |
| Nitroethane | 4.5 | 31.3 | |
| Methyl propyl ketone | 4.3 | 33.87 | |
| Benzyl alcohol | 3.5 | 39 | |
| Aniline | 3.4 | 42.9 | |

The data in Table 1 can be analyzed based on water solubility and surface tension of the solvents. The aqueous solubility of solvents determines the kinetics of solvent exchange that affects the phase separation (i.e., precipitation) of the polymer, and the surface tension determines the spreading of solvent around the aqueous droplet.

1. Solvents with High Water Solubility (50% and Higher)

For solvents with very high water solubility, such as acetic acid, acetone, N,N-dimethylacetamide (DMAC), N-methylpyrrolidone (NMP), and tetrahydrofuran (THF), solvent exchange occurs very fast at the solvent-water interface, and all PLGA polymer tends to become fine, individual precipitates rather than forming a polymer membrane around the aqueous droplet. If the polymer membrane is formed, then the surface of the polymer membrane is usually not smooth. For example, PLGA dissolved in acetic acid (with surface tension of 27.4 mN/m) forms the polymer membrane (i.e., capsule) on aqueous droplets, but the surface of the capsule is very rough due to fast solvent exchange. Solvents with very high water solubility but with relatively high surface tension, e.g., N-methylpyrrolidone (surface tension of 40.7 mN/m) and N,N-dimethylacetamide (surface tension of 32.4 mN/m), usually do not result in formation of continuous PLGA membrane on the aqueous droplet, but formation of discrete individual polymer precipitates separated from the aqueous droplet surface. This is most likely due to the high surface tension preventing the solvent from wrapping around the aqueous droplet. Thus, lowering the surface tension by adding excipients, e.g., surfactants, to the solvent can result in formation of a continuous PLGA membrane on the surface. It appears that a surface tension for the polymer solvent of 30 mN/m is a threshold value, above which the solvent may not spread well on the aqueous droplet. Therefore, it is generally preferred, but not necessarily required, for the solvent to have a lower surface tension, e.g., less than about 30 mN/m. Solvents with high water solubility are generally good for making microcapsules when aqueous droplets are contacted directly with the polymer dissolved in such solvents.

2. Solvents With Medium Water Solubility (5%–50%)

Those solvents that dissolve in water with solubility of 5–50% do not mix with water as quickly as other solvents with higher water solubility. Accordingly, only a very small fraction of PLGA precipitates on the surface of aqueous droplets and, as solvent exchange continues to occur, a stable polymer membrane is formed on the aqueous droplet surface. This process results in formation of a smooth PLGA membrane shell. Solvents of this type are good for making microcapsules in the air using two different microdispensers before collecting them in water. Examples of this type of solvent include methyl acetate and ethyl acetate. Both solvents resulted in formation of polymer capsule membrane on the aqueous droplet. The surface tensions of methyl acetate and ethyl acetate are 24.1 mN/m and 23.75 mN/m, respectively, which are smaller than 30 mN/m. Solvents with relatively high surface tension, e.g., acetyl acetone (surface tension of 31.2 mN/m) and furfural (surface tension of 41.1 mN/m), do not result in formation of continuous PLGA membrane on the aqueous droplet, but formation of small discrete droplets of polymer solution on the aqueous droplet surface. This is most likely due to the relatively high surface tension preventing the solvent from wrapping around the aqueous droplet. It appears that the surface tension of 30 mN/m is again a threshold value above which the solvent cannot spread on the aqueous droplet. As above, the solvent surface tension can be lowered as desired by adding an excipient, such as a surfactant, to provide a continuous polymer membrane on the aqueous core surface. It is noted that methyl acetate (aqueous solubility of 24.4%) does not form microspheres, not to mention microcapsules, if conventional double emulsion techniques are used. Ethyl acetate with lower aqueous solubility (8%) resulted in multinuclear microcapsules by conventional double emulsion methods. The formation of microcapsules by the solvent exchange method is a unique and new way of utilizing these solvents to prepare mononuclear microcapsules.

3. Solvents with Low Water Solubility (<5%)

The ability of those solvents with water solubility less than 5% to form a polymer membrane around the aqueous droplet depends on the surface tension. For example, benzyl alcohol (aqueous solubility of 3.5% and surface tension of 39.0 mN/m) does not allow formation of stable polymer membrane around the aqueous droplet. Instead, the solution resulted in formation of fine, individual polymer precipitates on the aqueous droplet. This is mainly due to relatively high surface tension of benzyl alcohol. On the other hand, methylene chloride (aqueous solubility of 1.3% and surface tension of 27.9 mN/m) can form the polymer membrane on the aqueous droplets, although the formation of polymer membrane is not as easy as other solvents with higher aqueous solubility. Again, the surface tension of approximately 30 mN/m appears to be a threshold value for formation of microcapsules. The inherent surface tension for a solvent can be lowered as desired by employing a suitable excipient, e.g., surfactant.

According to the data obtained so far, the solvents with water solubility of 50% and higher, in general, result in formation of fine polymer precipitates rather than formation of stable polymer membrane on the aqueous droplet. Acetic acid, however, resulted in formation of polymer membrane around the aqueous droplet, but the formed membrane was turbid white, indicating formation of polymer precipitates. For solvents with water solubilities between 5% and 50%, those with surface tension lower than 30 mN/m usually showed the formation of stable, transparent polymer membrane on the aqueous droplet. When the water solubility of solvent becomes smaller than 5%, solvent exchange occurs too slowly for effective formation of microcapsules by the solvent exchange method. Those solvents with water solubility less than 5% are more suitable for making microspheres by conventional methods, such as solvent evaporation and solvent extraction. They, however, still can be used in the solvent exchange method.

A manufacturing method of the present invention is particularly preferred for the microencapsulation of proteinaceous drugs. Exemplary of such drugs are insulin, somatostatin, luteinizing hormone releasing hormone (LHRH) and a derivative of LHRH, prolactin, adrenocorticotropic hormone (ACTH), growth hormone (GH), thyroid-stimulating hormone releasing hormone, melanocyte-stimulating hormone (MSH), luteinizing hormone (LH), palipresin, calcitonin, oxytocin, accessory thyroid hormone, gastrin, tetragastrin hydrochloride, glucagon, pancreozymin, cholecystokinin, angiotensin, human placental lactogen, human chorinic gonadotropin (HCG), enkephalin, endorphin, keutorphin, interferon, interleukin (I, II, III), tumor necrotizing factor (TNF), tuftsin, thymopoietin, thymosin, thymostimulin, thymic humoral factor, blood thymic factor, colony stimulating factor, motiline, deinorphin, bompesin, neurotensin, cerulein, bradykinin, urokinase, asparaginase, kallikrein, substance P, nerve growth factor, blood coagulating factor, lysozyme chloride, polymyxin B, colistin, glamicidin, bacitracin, and the like. Others will be apparent to the skilled practitioner.

Advantages of the Solvent Exchange Method

There are many advantages of the solvent exchange method over conventional methods, such as solvent extraction and solvent evaporation techniques. Since the solvent exchange method is a one-step process, it is much simpler than any other current microencapsulation techniques. Thus, the process can be scaled up without any difficulty. The simplicity also brings down the overall cost of microcapsule production significantly.

In solvent exchange methods, the solvent for polymers can be chosen with more flexibility. Conventional double emulsion solvent extraction or solvent evaporation methods are limited to solvents that are not too hydrophilic so that the emulsion can be formed and are not too hydrophobic so that emulsion droplets may not stay too long in a liquid state. It was found that drug partitioned into the aqueous phase as long as the emulsion droplets were in a liquid, non-precipitate state (32). Thus, solvents that could be successfully used in conventional methods were limited to only a few solvents; practically to methylene chloride. This is one of worst disadvantages of conventional emulsion methods, since methylene chloride is a possible carcinogen and its residual amount should be strictly controlled under the limit.

On the other hand, the above-mentioned limitations do not apply to solvent exchange methods. First, high water solubility of solvent is not a problem since the solvent exchange method does not depend on formation of emulsion. Low water solubility of solvents is not a limiting factor either in the solvent exchange method, since the absolute amount of solvent to be removed is much less than in conventional emulsion methods. Furthermore, the encapsulation efficiency can be markedly improved in the solvent exchange method because the polymer membrane is formed very fast on the surface of aqueous microdroplets leading to the minimum loss of the loaded drugs. As shown in the literature, drug loss across the droplet interface occurs only during the first minutes before polymer precipitation (32). As long as the microparticle, which can have any shape and is typically less than about 1 mm in size, is 'closed' by precipitation of polymer, any further diffusion of drug into the aqueous phase would be hindered. In the solvent exchange method, the precipitation would not only occur very quickly because the absolute amount of solvent is small, but also the precipitation rate can be controlled by proper selection of solvents. Thus, high encapsulation efficiency can be obtained in the solvent exchange method regardless of the water solubility of drugs.

In the solvent exchange method, the thickness of the polymer capsule membrane can be controlled by adjusting the polymer concentration in the solvent: the higher the polymer concentration, the thicker the membrane. Those microcapsules with a thicker polymer membrane will result in higher lag time before the loaded drug is released. Also, by mixing the microcapsules with different polymer thicknesses, the release rate can be controlled from zero-order to pulsatile release.

The solvents used in the solvent exchange method are hydrophilic organic solvents that mix with water well or are relatively soluble in water and generally much less toxic than those solvents commonly used in conventional methods. One of the preferred solvents for the solvent exchange method is acetic acid, which is safe for humans. Acetic acid is classified by the FDA as a Class 3 solvent, which has low toxic potential to man and requires no health-based exposure limit. Acetic acid that may remain in the microcapsules can be removed quite easily during freeze drying of microcapsules. There is no need to be concerned with the toxicity of the residual organic solvent.

Another advantage of the present invention is that it is a simple method of making mononuclear microcapsules, which provides protective effects for the drug entities inside the core by minimizing the contact of the drug with the polymer matrix. At the same time, it provides a good control over the release rate by the erosion of the polymer capsule membrane. The exposure of the protein drug entity to the solvent is much shorter than in conventional methods and is localized only on the core surface. Thus, it is possible to minimize protein denaturation, if any, due to exposure to solvents during capsule formation. It is a further advantage of this invention that it eliminates deleterious conditions affecting drug stability during the manufacturing process, such as exposure to high shear stress and the large interface between organic and aqueous solvents. Another advantage is the capability of precise microcapsule fabrication by the method of microdroplet jetting. Another advantage of this invention is the simplicity of a single step allowing easy scale-up manufacturing.

The invention is now described with reference to certain examples for purposes of illustration and explanation, but not by way of limitation. Obvious variations will be apparent to those skilled in the art.

EXAMPLE 1

Macrocapsules are made by the solvent exchange method using a simple syringe/needle system as shown in FIG. 1. When drops of aqueous protein solution (e.g., albumin or gelatin) are introduced into the polymer solution (e.g., PLGA dissolved in acetic acid), the droplets remain spherical due to the high surface tension of the water. PLGA polymer forms a layer surrounding a protein droplet instantaneously. This is because acetic acid is highly miscible with water and thus, acetic acid diffuses into the outer layer of the protein droplet and at the same time water diffuses out of the droplet to the PLGA/acetic acid solution. The PLGA layer becomes thicker as more time is allowed for solvent exchange. If the formed macrocapsules, moistened with acetic acid, are picked up by forceps and transferred to water, all the PLGA in the acetic acid layer associated with the droplets precipitates immediately to form a thicker coating.

In one embodiment of the method depicted in FIG. 1, only protein drug molecules located on the outer edge of the droplets are exposed to PLGA/acetic acid. This limits the possible denaturation of proteins at the solid/liquid interface. It is possible that some proteins can maintain their bioactivity even after brief exposure to PLGA/acetic acid. This is possible especially when the protein solution contains buffering agents to maintain the desired pH while the aqueous layer on the microdroplet surface mixes with acetic acid. In FIG. 1, PLGA deposits onto the protein core immediately due to fast dilution of acetic acid around the aqueous protein core. Since the reservoir space in the center (protein core in FIG. 1) is not occupied by PLGA or solvent, the total space for loading of protein drugs is maximized by this method. This has been one of the unique advantages of reservoir devices, such as microcapsules, over other matrix devices, such as microspheres prepared by solvent extraction or evaporation methods.

Macrocapsules formed using the aforementioned solvent exchange process shown in FIG. 1, wherein the capsules were made by injecting gelatin droplets using a syringe, can be in the millimeter range. The size can be made in the micrometer range using nozzles or any other devices that can generate microdroplets. One of the capsules was selected to break open for visual inspection. The hollow space inside the macrocapsule can be used as a reservoir for one or more protein drugs. The same method can be used to produce microcapsules in large quantities for protein drug delivery. If protein drugs have to be protected from contact with acetic acid, e.g., to avoid denaturation, the protein drug core can be covered with a protecting layer that shields the protein drugs from the acetic acid, which is described hereinbelow.

EXAMPLE 2

Figure 2:
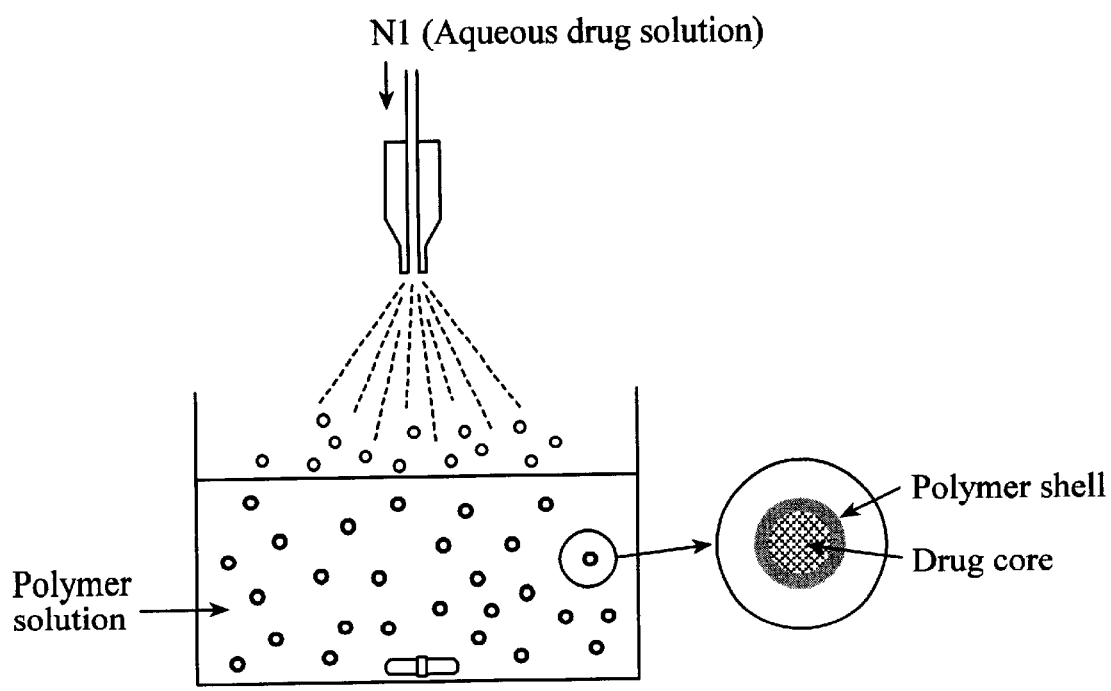
FIG. 2 depicts formation of microspheres or microcapsules using a single nozzle system. The polymer forms a shell around the microdroplets by instantaneous solvent exchange between the water and polymer solvent phases.

The preparation of microcapsules using the solvent exchange method requires the use of devices that generate microdroplets. Microdroplets can be made either with nozzles or microvolume dispensing instruments based on inkjet head technology. Inkjet head technology is well known and there is little to optimize once the instrument is set up, as described below. For the nozzle approach, two different types of nozzles can be used: a plain, single orifice nozzle or a coaxial nozzle. As shown in FIG. 2, a plain nozzle can be used to make microcapsules. In this method, aqueous protein solution (delivered through N1) is atomized into microdroplets that can be collected in the polymer solution, e.g., PLGA dissolved in acetic acid. The microdroplets falling into the polymer solution form a polymer shell immediately on the surface due to instantaneous solvent exchange between the polymer solvent and water.

EXAMPLE 3

The thickness of the polymer shell is dictated by the amount of water present in each microdroplet and the concentration of polymer in the solvent. One way of making a thicker PLGA shell is to phase separate PLGA from the solution by lowering the solvent quality, as commonly done in the coacervation approach. In this case, acetic acid, N,N-dimethyacetamide, DMSO, or ethyl acetate, for example, in the bulk solution is diluted with a non-solvent for PLGA, such as ethanol, after the microcapsules have been initially formed. Adding ethanol directly to the PLGA/acetic acid solution results in immediate precipitation of PLGA in the bulk solution. Slow addition of a gradient of ethanol/acetic acid or water/acetic acid results in accumulation of PLGA on the already formed PLGA shell. This produces microcapsules with a thicker PLGA shell, the thickness of which can be controlled by PLGA concentration and the rate of lowering the solvent quality in the PLGA solution.

EXAMPLE 4

Figure 3:
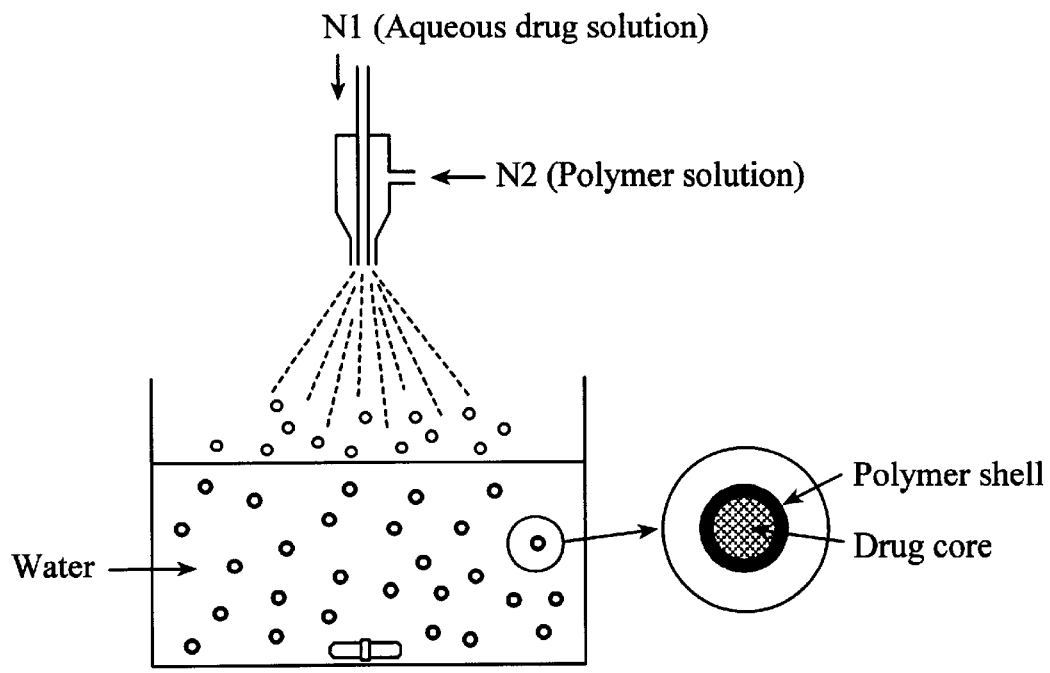
FIG. 3 depicts preparation of microspheres or microcapsules using a coaxial nozzle system. The polymer shell starts forming immediately after the drug core is released from the nozzle and shell formation is substantially complete upon contact with the bulk water.

The co-axial nozzle approach is designed to make the solvent exchange method even simpler. As shown in FIG. 3, the aqueous protein solution microdroplets produced by the inner nozzle N1 are covered by the PLGA/solvent, e.g., acetic acid or ethyl acetate, solution (supplied through the outer nozzle (N2 in FIG. 3). The PLGA starts forming the shell immediately. At the same time, the microdroplets fall into water and the remaining PLGA in solvent precipitates on the shell to complete the microcapsule formation. This method is much simpler than the plain nozzle method and is potentially a very powerful approach for scale-up. While it is simpler and more convenient that the plain nozzle method, the coaxial nozzle method requires more fine-tuning. In this method, the thickness of the PLGA shell is mainly controlled by the PLGA concentration in the PLGA solution and volume of PLGA/solvent introduced to each microdroplet. In the preparation of microcapsules using a coaxial nozzle system, the polymer shell is formed right after the protein core is released from the nozzle and the shell formation is substantially complete by the time the droplet contacts the bulk water.

EXAMPLE 5

Figure 4:
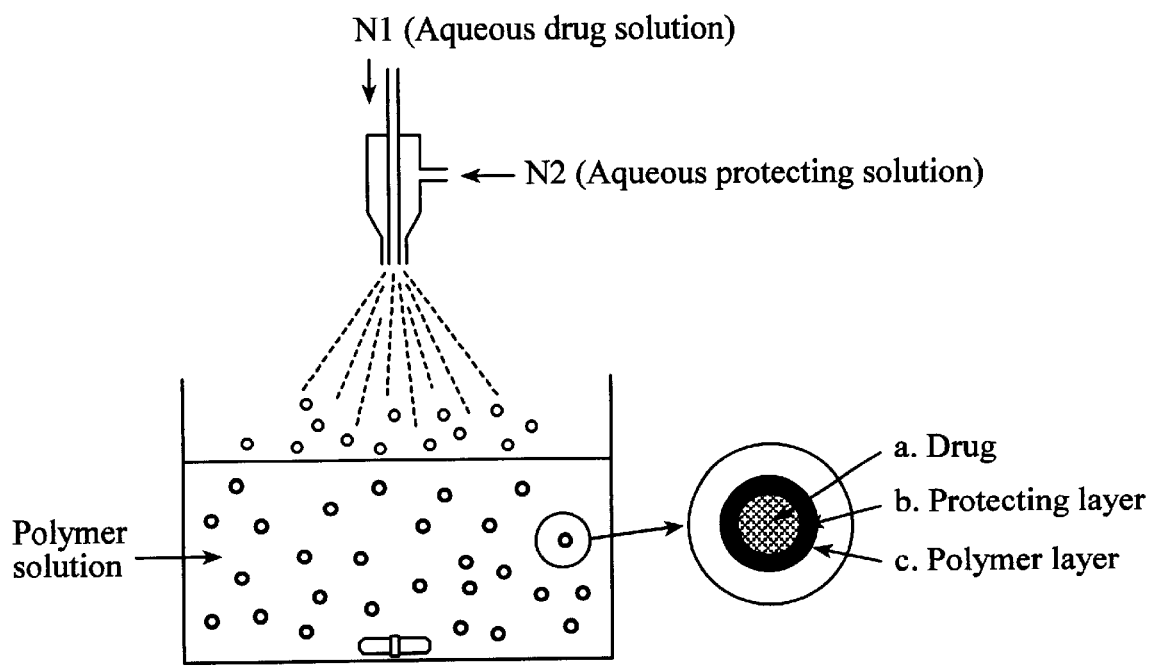
FIG. 4 depicts a variation of the apparatus shown in FIG. 2, wherein a protecting layer forms around the drug core prior to deposition of the polymer shell.

It is possible that a fraction of the drug molecules in the core of a microcapsule may lose bioactivity by being exposing to the polymer solvent, which diffuses into the outer edge of the aqueous core. If this becomes a concern, the drug core can be coated with a protecting layer as shown in FIG. 4. As illustrated, an aqueous drug solution is introduced into the inner orifice of the coaxial nozzle (N1). A protecting solution containing protecting polymers (e.g., gelatin, alginic acid, carrageenan, chitosan, or thermosensitive synthetic polymers) is introduced (N2) via the outer orifice to coat the drug-containing microdroplets. Thus, protein microdroplets consist of the protein drug core (a) and the protecting layer (b) in FIG. 4. When the formed microdroplets are dropped into the polymer-containing solution, the polymer, e.g., PLGA, starts forming a secondary layer (c) over the protecting layer. In this approach, a protein drug is not exposed to potentially denaturing solvent at all. This is also a useful approach for those drugs that are highly sensitive to small changes in pH.

To prevent excessive pH lowering by polymer solvent during encapsulation, basic additives, such as $MgCO_3$, $Mg(OH)_2$, or $ZnCO_3$, can be added to the aqueous drug solution. Of these, $MgCO_3$ is the most water-soluble, and thus is generally better than the other two for maintaining the pH. On the other hand, $ZnCO_3$ may also be useful, since zinc ions are known to stabilize many protein drugs including human growth hormone (hGH) and erythropoietin (11). Sometimes it may be necessary to make a drug core mechanically strong for easier handling, which can be done by adding polymers (either natural or synthetic) to the drug solution. Typically, polymers that form a gel immediately upon a change in environment are preferred. For example, sodium alginate becomes a gel almost instantaneously upon contact with calcium ions. Thus, by adding sodium alginate to an aqueous protein solution and adding calcium ions to the polymer (e.g., PLGA/acetic acid or ethyl acetate) solution, the protein core can be converted into a gel before the polymer shell if formed on the surface. This technique makes microcapsules much stronger than in the absence of an alginate-calcium system. Other polymer systems that can be used for this purpose include anionic gelatin-poly(L-lysine), chitosan-anionic polysaccharide, and carrageenan-salt combinations (10). It is noted that the gel systems used for improving mechanical strength can also be used to control the drug release rate, even after the polymer shell is degraded. Thus, a gel system provides dual beneficial effects.

EXAMPLE 6

Figure 5:
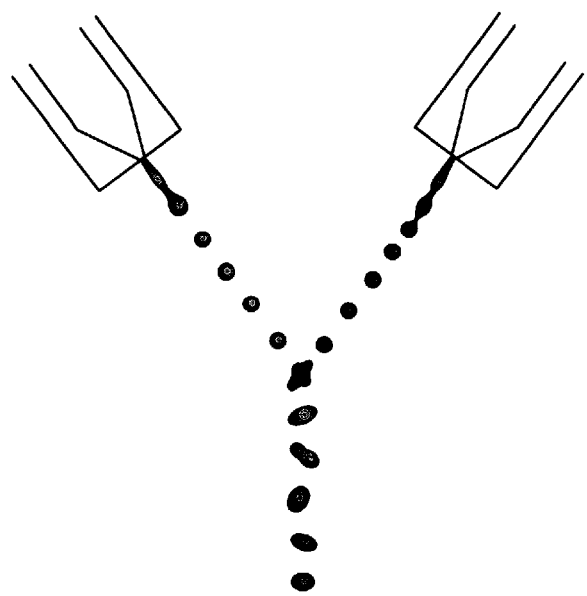
FIG. 5 depicts one aspect of the invention in which microdispensers, e.g., of the inkjet type, are employed to form microspheres or microcapsules by solvent exchange. A first microdispenser generates aqueous microdroplets and the second generates microdroplets of polymer-dissolved solvent. The two microdispensers are aligned in such a way that the two different microdroplets come in contact in air. This illustration is based on photographs obtained using stroboscopic illumination for clear presentation.

Microcapsules can also be prepared using a microdispenser, similar to an inkjet device (24–26). A method of producing microencapsulated droplets entails producing discrete drops in air of the material to be encapsulated and the material that will form the capsule, e.g., using two different microdispensers (FIG. 5). The drops are allowed to come into contact in air before they fall into a receiving vessel. The difference in surface tension between the outer capsule material solution (e.g., PLGA dissolved in acetic acid or methyl acetate) and the inner solution of material to be encapsulated (e.g., aqueous protein solution) allows the outer solution to engulf the inner solution. Specifically, the outer solution should have a lower surface tension so that contact between the two drops lowers surface tension locally on the surface of the inner solution, which sets up a Marangoni (or surface tension driven) flow drawing the outer fluid around the inner fluid. As shown from examples in Table 1, polymer solvents with a surface tension less than 30 mN/m are preferred. After the outer fluid has had sufficient time (typically several microseconds to several milliseconds or longer depending on the sizes of the drops and relative surface tensions) to coat the inner fluid, the microcapsule can be solidified. In this embodiment, the capsule can be solidified by allowing it to fall into a pool of water laden with surfactant to aid the drop falling into the pool. The exact chemistry of the microcapsule will in general determine the particular method by which the outer fluid is solidified. Microcapsules produced in this manner are essentially monodisperse in both volume of the encapsulated liquid and thickness of the encapsulation coating.

One apparatus for generating microencapsulated drops consists essentially of a continuous ink-jet (CIJ) nozzle, which produces a steady stream of discrete droplets and a plate accommodating a film of polymer solution. A representative CIJ nozzle is described in U.S. Pat. No. 3,596,275 (issued to Sweet). The nozzle is preferably a drawn glass capillary with an outlet orifice ranging from 30 μm in diameter to 60 μm in diameter, but the nozzles can be of any size and geometry. The nozzle is fed with a hydrophilic core material containing a drug under sufficient pressure that a liquid jet emanates from the nozzle orifice. In this embodiment, the nozzle can be fed with a syringe pump, but any method can be used to generate the appropriate driving force. In the absence of external force, a liquid jet breaks into discrete droplets in a random fashion with a variation in size and position of each droplet. It is thus important to control the breakup of the liquid jet so that the droplets are well defined in sizes and positions. This control over drop formation can be accomplished by perturbing the jet periodically (in this embodiment sinusoidal waveforms are used), which causes the drops to be monodisperse and spaced very regularly. The perturbation can be accomplished by applying a periodically varying voltage to a piezoelectric transducer, which consists of a sleeve concentric with and bonded to the outside of the glass capillary forming the nozzle. Application of the voltage signal causes the transducer to periodically contract and expand imparting a pressure perturbation to the liquid inside the nozzle which in turn forces the jet to break into regular drops. In this embodiment, the nozzle is operated at the same frequency by a single piezo driver/function generator. The nozzles are positioned so that the drops exiting from each orifice collide (FIG. 5) and upon collision, the outer fluid engulfs the inner fluid producing a microcapsule. The inner fluid (i.e., hydrophilic core solution) having a higher surface tension maintains its spherical shape whereas the outer fluid (i.e., polymer solution) of relatively lower surface tension wraps around the hydrophilic core. Right after contact between the two microdroplets, the water miscible solvent begins to mix with water of the core particle, leading to a slight decrease of solvent quality and deposition of polymer coat on the surface of the core particle to produce a mononuclear microcapsule. The resulting microcapsules are collected in a water bath containing a surfactant to allow further extraction of the solvent and hardening of the microcapsules. Surfactants are included to reduce the resistance against introducing the microcapsules into the water bath and to prevent aggregation of the formed microcapsules. The microcapsules can be collected by centrifugation or filtration and then freeze dried.

Drop-on-demand nozzles (DOD) and associated technologies can also be used to deliver the microdroplets (13). Exemplary devices are described by U.S. Pat. No. 3,683,212 (issued to Zoltan) and U.S. Pat. No. 3,946,398 (issued to Kyser et al.).

This method minimizes exposure of the drug molecules to the solvent and high shear stress, which are disadvantages of conventional methods. Another advantage of this method is that precise control of the particle size and size distribution can be obtained. Since a homogeneous particle size is one of the requirements for a desired release rate, the size distribution has been an important issue for controlled drug delivery. However, conventional methods have not been able to provide appropriate means to permit narrow particle size distribution. The present invention, therefore, affords a simple and easy solution using microdispensers controlled by piezoelectric transducers.

The droplet radius, $r_d$, is known to be governed by three variables, i.e., the flow rate of jetted solution, the orifice size of the nozzle, and the acoustic frequency such that:

$$r_d = (3r_j^2 v_j/4f)^{1/3}$$

where $r_j$ is the orifice radius, $v_j$ is the solution flow rate, and f is the acoustic frequency, all of which are well in hand (33). Now that commercial microdispensers of different orifices are available from 30 μm to 60 μm, the orifice size can be conveniently varied. In addition, the flow rate and frequency can be easily optimized by use of a syringe pump and a piezoelectric transducer. The particle size distribution obtained is substantially homogeneous. Commercial suppliers of suitable microdispensers include MicroFab Technologies, Inc. (Plano, Tex.).

EXAMPLE 7

In another embodiment, a single microdispenser can be used to produce microdroplets of an aqueous protein solution and the formed aqueous microdroplets can be passed through a mist of microdroplets of capsule material solution (e.g., PLGA dissolved in acetic acid or methyl acetate). The mist of encapsulation material can be generated with an atomizing nozzle (e.g., ultrasonic atomizing nozzle with ultrasonic generator). The size of the microdroplets generated can be varied from less than 1 μm to more than the size of the aqueous droplets. By controlling the density and size of the microdroplets of the capsule material solution, the thickness of the polymer capsule can be easily controlled. The mist of capsule materials can be confined in a chamber so that only aqueous microdroplets passing through the chamber can interact with them. The aqueous microdroplets coated with polymer capsule are then collected in a water bath. Suitable commercial atomizing nozzles are available from SonoTek Corp. (Milton, N.Y.).

EXAMPLE 8

Under a nozzle assembly, such as that shown in FIG. 2, a stainless steel plate with a hole that can accommodate a film of polymer solution is placed. The plate is connected to a reservoir of polymer solution. The polymer solution is provided continuously to near the hole, over which a stainless steel needle moves back and forth to spread the polymer solution making a film. A hydrophilic core material containing drug molecules is jetted onto the film as described above. Liberated core droplets pass through the film of polymer solution in the hole. Upon contact between the hydrophilic core droplet and the film of polymer solution, the water miscible solvent begins to mix with water of the core droplet, leading to a slight decrease of solvent quality and deposition of polymer coat on the surface of core particle to produce mononuclear microcapsules. The resulting microcapsules are collected in a water bath containing a surfactant, to allow further extraction of the solvent and hardening of the microcapsules. Surfactants are included in order to reduce the resistance against introducing the microcapsules into the water bath and to prevent aggregation of the microcapsules.

EXAMPLE 9

A microcapsule can be fabricated using a concentric nozzle. It has been shown that microcapsules can be produced using a concentric nozzle controlled by a piezoelectric transducer (34). By varying the time to send a signal to the inner and outer nozzles, respectively, a microcapsule can be made at the end of the concentric nozzle. Briefly, the microcapsules are made by jetting the first liquid (A) from the outer nozzle and the second liquid (B) from the inner nozzle. Jetting begins with the liquid A through the outer nozzle by the piezoelectric transducer. After a certain period from the beginning of jetting of the liquid A, the liquid B is subsequently jetted through the inner nozzle also under the control of the piezoelectric transducer. Since the liquid A began jetting first, the liquid B is jetted into the liquid A, therefore the liquid B is engulfed by the liquid A to make a layered droplet as jetting proceeds. Shortly after the layered droplet begins to form, the piezoelectric body pauses jetting of the liquid B, and subsequently pauses jetting of the liquid A. These pause signals allow a temporary return of each solution inside the nozzle to the reservoirs, thereby separating the microcapsule produced outside the nozzle tip. After jetting a microcapsule, the whole procedure repeats from the beginning to produce another microcapsule under a programmed control. This type of nozzle system can be used to practice solvent exchange. The liquid A from the outer nozzle and the liquid B can be PLGA solution and a protein drug containing hydrophilic core material, respectively. As soon as the two liquids contact at the tip of the nozzle, the water miscible solvent of the polymer solution begins to mix with water of the core material, leading to a slight decrease of solvent quality and deposition of polymer coat on the surface of core material. A timed jetting signal separates the coated particle from the tip of the nozzle as a microcapsule, which is collected in the water bath containing a surfactant, to allow further extraction of the solvent and hardening of the microcapsules.

This system can be modified by flowing a carrier stream around the stationary concentric nozzle in order to further reduce the particle size. A current stream has been used previously in combination with a small orifice nozzle to achieve precise control of particle sizes and effective particle size distribution in producing monolithic microspheres (33). In another instance, the carrier stream that is not miscible with polymer solution serves as a shearing force to the microcapsules forming at the tip of concentric nozzle (35). In this case, however, the microcapsules range in diameter from 300 μm to 600 μm.

The above mentioned concentric nozzle system controlled by a piezoelectric transducer can be used along with a carrier stream as follows. While a hydrophilic core solution and a polymer solution are pumped through an inner nozzle and an outer nozzle of a concentric nozzle, respectively, a carrier stream flows around the emerging microcapsules. The carrier stream is not miscible with polymer solution and its surface tension and density are lower than for water. When the velocity of the carrier stream is higher than the polymer stream, the carrier pulls on the polymer, focusing it into a jet of reduced diameter. In this manner, the diameter of droplets is reduced as a function of the orifice diameter and the relative flow rates of the polymer solution and the carrier stream. The stream flows into a water bath, where the carrier liquid stays on top of water but the microcapsules escape the carrier liquid and go into the bulk water. Microcapsules collected in the water bath then can be hardened through further solvent exchange.

EXAMPLE 10

Hydrophilic cores containing drug molecules can be prepared separately prior to the coating process. An aqueous solution containing the drug substance and protective core material is sprayed into a continuous bath. Any method can be used to produce core particles of desired size range. When the core material is capable of physical cross-linking depending on the change of external conditions such as pH, temperature, ionic strength, or the presence of other polymer, it is possible to collect core particles separately prior to polymer coating by controlling one of the conditions in the collecting bath. For instance, hydrophilic core particles can be conveniently made by cross-linking of alginate chains in the presence of calcium ions in the water bath. The resulting core particles are collected by centrifugation or filtration and subsequently washed with the same solvent that is used for the polymer solution. Polymer solution is added to the core particles with stirring until the particles completely contact polymer solution. As soon as the core particle and polymer solution contact each other, the water miscible solvent of the polymer solution begins to mix with water of the core particles, leading to a slight decrease of solvent quality and deposition of polymer coat on the surface of core particles. The precipitation is expedited by addition of non-solvent for the polymer to the bulk polymer solution. A gradient of non-solvent and solvent is added with increasing concentration of non-solvent, which results in further deposition of polymer on the surface of the particles. The thickness of the polymer coating can be controlled by varying the mixing rate of non-solvent to the gradient and the addition rate of the gradient to the bulk polymer solution. The resulting microcapsules are washed with non-solvent and/or then with distilled water and dried.

EXAMPLE 11

Albumin can be microencapsulated using the solvent exchange method and the release profile from microcapsules has been examined. In this study, 4 ml of aqueous solution containing 500 mg of bovine serum albumin (BSA) and 40 mg of sodium alginate is sprayed into 30 ml of 0.15 M $CaCl_2$ aqueous solution. The resulting particles are collected by filtration after curing for 10 min in the $CaCl_2$ solution and subsequently washed with acetic acid or N-methylpyrrolidone. PLGA (50:50) solution in glacial acetic acid or N-methylpyrrolidone (10/w %) is added to the particles with stirring for 5 min. A gradient of ethanol and glacial acetic acid (or N-methylpyrrolidone) is added with increasing concentration of ethanol, which results in precipitation of polymer on the surface of the particles. At the same time, excessive polymer is removed from the solution. Alginate particles coated with PLGA are washed with ethanol and then with distilled water for hardening of the polymer coating and freeze-dried.

Figure 6:
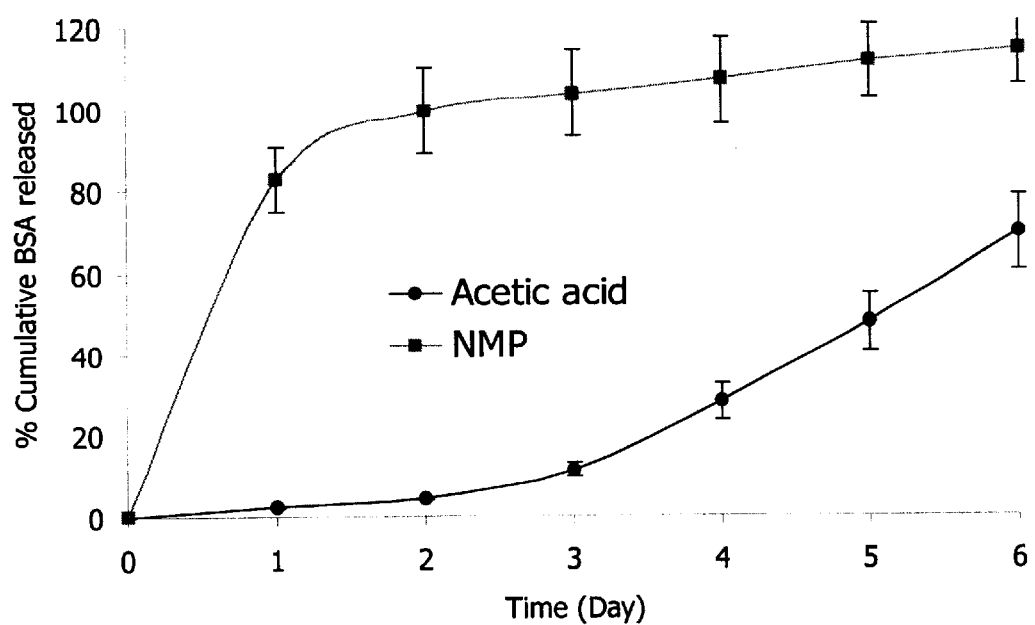
FIG. 6 illustrates the cumulative rate of in vitro release of bovine serum albumin (BSA) from microcapsules prepared by the solvent exchange method of the present invention using two different solvents (acetic acid and N-methylpyrrolidone).

To determine the release profile of albumin out of the microcapsules, dried microcapsules are weighed and placed in a vial containing 3 ml of pH 7.4 buffer solutions. The vials are shaken at 37° C. Supernatant is completely removed at timed intervals for measurements of released albumin and fresh buffer is replenished. FIG. 6 depicts the cumulative in vitro release of BSA from microcapsules prepared using this method of the present invention.

EXAMPLE 12

Solvents suitable for a solvent exchange method of the present invention utilizing PLGA can be primarily selected by having a solubility parameter in the range of 16–24 $MPa^{1/2}$. Among the 34 solvents tested, 14 solvents turned out to be good solvents for PLGA and 10 were non-solvents. The remainder of the solvents showed an intermediate performance. For better prediction of polymer solubility, partial solubility parameters introduced by Hansen (36) are plotted on a triangular graph following the Teas method (37). Hansen's multicomponent solubility parameters are described as:

$$\delta^2 = \delta_d^2 + \delta_p^2 + \delta_h^2$$

where $\delta$ is the total solubility parameter, $\delta^d$ is the contribution from dispersion force, $\delta_p$ polar interaction, and $\delta_h$ hydrogen bonding. Fractional parameters are calculated as:

$$f_i = 100\delta_i/(\delta_d + \delta_p + \delta_h)$$

where i=d, p, or h.

Figure 7:
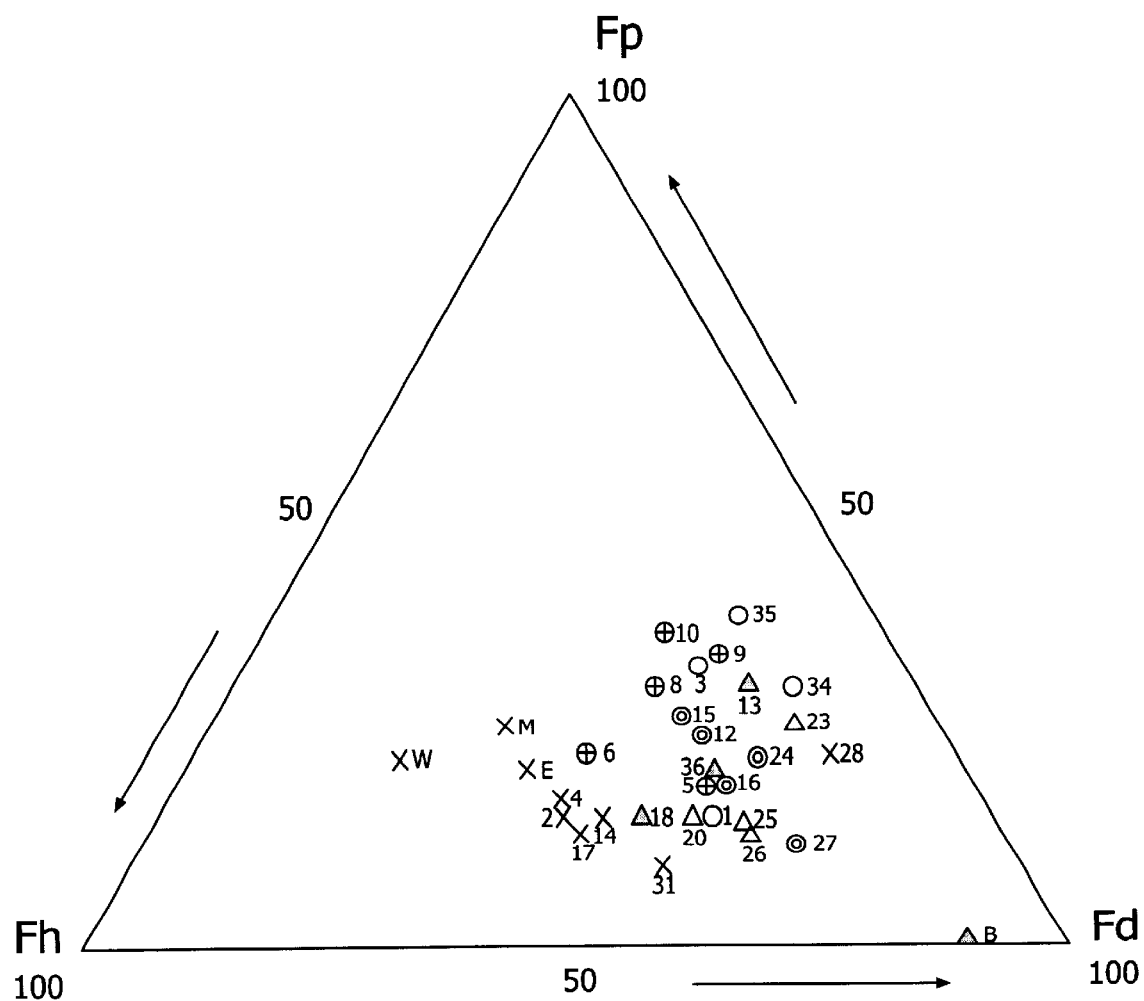
FIG. 7 depicts a plot of various polymer solvents as a function of the fractions of their respective dispersion force ($F_d$), polarity ($F_p$), and hydrogen bonding ($F_h$). (O) good solvent; (⊚) good solvent forming transparent membrane; (⊕) good solvent forming while precipitate; (▲) intermediate good solvent; (△) intermediate poor solvent; and (X) poor solvent. (B) benzene; (E) ethanol; (M) methanol; and (W) water. (1) n-butyl amine; (2) isopropyl alcohol; (3) acetone; (4) 1-propanol; (5) tetrahydrofuran; (6) acetic acid; (8) N,N-dimethylacetamide; (9) N-methylpyrrolidone; (10) dimethyl sulfoxide; (12) methyl acetate; (13) methyl ethyl ketone; (14) 2-butanol; (15) ethyl formate; (16) ethyl acetate; (17) 1-butanol; (18) benzyl alcohol; (20) isopropyl acetate; (23) methyl isobutyl ketone; (24) methylene chloride; (25) isobutyl acetate; (26) n-butyl acetate; (27) chloroform; (28) methyl amine ketone; (31) 1-octanol; (34) acetylacetone; (35) furfural; (36) butyraldehyde.

When solvents (of which Hansen parameters (38) are available) are plotted by using fractional parameters on a triangular graph, good solvents are localized in a region as shown in FIG. 7. Solvents that dissolve PLGA and form the PLGA membrane on the aqueous droplet have low $F_p$ and $F_h$, but high $F_d$. Of the good solvents, those making transparent membrane and white precipitate were marked separately. The trends approximately correspond to water solubility. From such a triangular graph, any solvent that may be placed in the region including #12, 15, 16, and 24 is expected to make microcapsules with transparent polymer membranes. The solvent power increases towards the center of the solubility boundary. FIG. 7 suggests that one can select suitable solvents for the solvent exchange method utilizing PLGA and other polymers by plotting the dispersion force, polarity, and hydrogen bonding components on a triangular graph. This graph method also provides guidance for the selection of solvent mixtures. The partial solubility parameters for solvent mixtures, $\delta_{i,m}$, are calculated as:

$$\delta_{i,m} = \phi_1 \delta_{i,1} + \phi_2 \delta_{i,2}$$

where i=d, p, or h, and the $\phi$'s are the volume fractions of the component solvents.

The present invention has been described hereinabove with reference to particular examples for purposes of clarity and understanding rather than by way of limitation. It should be appreciated, however, that certain improvements and modifications can be practiced within the scope of the appended claims. For instance, albumin can be substituted generally with one or more other water-soluble polymers, such as sense and anti-sense oligonucleotides, genes, polysaccharides, and proteins. Likewise, PLGA can be substituted with other water-insoluble biodegradable polymers without limitations.

REFERENCES

The pertinent disclosures of the following references are incorporated herein by reference.

1. Arshady, R.: Microspheres, microcapsules and liposomes. General concepts and criteria, Arshady, R., Eds., Citrus Books, London, United Kingdom, 1999, 11–45.
2. Thies, C.: A survey of microencapsulation processes, Benita, S., Eds., Marcel Dekker, Inc., New York, N.Y., 1996, 1–19.
3. Benoit, J. -P., Marchais, H., Rolland, H., and Velde, V. V.: Biodegradable microspheres: Advances in production technology, Benita, S., Eds., Marcel Dekker, Inc., New York, N.Y., 1996, 35–72.
4. Allemann, E., Gurny, R., and Doelker, E.: Drug-loaded nanoparticles-preparation methods and drug targeting issues, *Eur. J. Pharm. Biopharm.* 39: 173–191, 1993.

5. Okada, H., and Toguchi, H.: Biodegradable microspheres in drug delivery, *Critical Review in Therapeutic Drug Carrier Systems* 12: 1–99, 1995.
6. Li, J. K., Wang, N., and Wu, X. S.: A novel biodegradable system based on gelatin nanoparticles and poly(lactic-co-glycolic acid) microspheres for protein and peptide drug delivery, *J. Pharm. Sci.* 86: 891–895, 1997.
7. Wang, N., and Wu, X. S.: A novel approach to stabilization of protein drugs in plga microspheres using agarose hydrogel, *Int. J. Pharm.* 166: 1–14, 1998.
8. Schwendeman, S. P., Tobio, M., Joworowicz, M., Alonso, M. J., and Langer, R.: New strategies for the microencapsulation of tetanus vaccine, *Journal of microencapsulation* 15: 299–318, 1998.
9. Zhou, S., Deng, X., and Li, X.: Investigation on a novel core-coated microspheres protein delivery system, *J. Controlled Rel.* 75: 27–36, 2001.
10. Park, K., Shalaby, W. S. W., and Park, H.: Biodegradable Hydrogels for Drug Delivery, Technomic Publishing co., Inc. Lancaster, P., 1993, pp.99–140.
11. Tice, T. R., and Lewis, D. H.: Microencapsulation process, U.S. Pat. No. 4,389,330, 1983.
12. Weert, M., Hennink, W. E., and Jiskoot, W.: Protein instability in plga microparticles, *Pharm. Res.* 17: 1159–1167, 2000.
13. Le, H. P.: Progress and trends in ink-jet printing technolog, J. Imaging Sci. Technol., 42: 49–62, 1998.
14. Mumenthaler, M., Hsu, C. C., and Pearlman, R.: Feasibility study on spray-drying protein pharmaceuticals: Rhgh and t-pa, *Pharm. Res.* 11: 12–20, 1994.
15. Maa, Y. -F., Nguyen, P. -A. T., and Hsu, S. W.: Spray-drying of air-liquid interface sensitive recombinant human growth hormone, *J. Pharm. Sci.* 87: 152–159, 1998.
16. Knutson, B. L., Debenedetti, P. G., and Tom, J. W.: Preparation of microparticulates using supercritical fluids, Cohen, S., and Bernstein, H., Eds., Marcel Dekker, Inc., New York, N.Y., 1996, 89–125.
17. Ghaderi, R., Artursson, P., and Carlfors, J.: Preparation of biodegradable microparticles using solution-enhanced dispersion by supercritical fluids (seds), *Pharm. Res.* 16: 676–681, 1999.
18. Johnson, O. L., and Tracy, M. A.: Peptide and protein drug delivery, in Encyclopedia of Controlled Drug Delivery, Mathiowitz, E., Eds., Jone Wiley & Sons, Inc., New York, N.Y., 1999, 816–833.
19. Sah, H.: Protein instability toward organic solvent/water emulsification: Implications for protein microencapsulation into microspheres, *PDA J. Pharm. Sci. Technol.* 53: 3–10, 1999.
20. Morlock, M., Koll, H., Winter, G., and Kissel, T.: Microencapsulation of rherythropoietin, using biodegradable plga: Protein stability and the effects of stabilizing excipients, *Eur. J. pharmaceutics Biopharm.* 43: 29–36, 1997.
21. Gombotz, W., Pettit, D., Pankey, S., Lawter, J. R., and Huang, W. J.: Prolonged release of gm-scf, U.S. Pat. No. 5,942,253, 1999.
22. Shah, S.: Biodegradable microparticles for the sustained delivery of therapeutic drugs, U.S. Pat. No. 6,020,004, 2000.
23. Benoit, J. -P., Richard, J., Fournier, E., and Liu, S.: Method for encapsulating active substances by coacervation of polymers in non-chlorinated organic solvent, PCT Int. Appl. 0,115,799,2001.
24. Peregrine, D. H., Shoker, G., and Symon, A.: The bifurcation of liquid bridges, J. Fluid Mech., 212: 25–39, 1990.
25. Zhang, X. and Basaran, O. A.: An experimental study of dynamics of drop formation, Phys. Fluids, 7: 1184–1203, 1995.
26. Wilkes, E. D., Philips, S. D., and Basaran, O. A.: Computational and experimental analysis of dynamics of drop formation, Phys. Fluids, 11: 3577–3598, 1999.
27. Blanco-Prieto, M. J., Besseghir, K., Zerbe, O., Andris, D., Orsolini, P., Heimgartner, F., Merkle, H. P., and Gander, B.: In vitro and in vivo evaluation of a somatostatin analogue released from plga microspheres, *J. Controlled Rel.* 67: 19–28, 2000.
28. Eliaz, R. E., and Kost, J.: Characterization of a polymeric plga-injectable implant delivery system for the controlled release or proteins, *J. Biomed. Mater. Res.* 50: 388–396, 2000.
29. Lambert, W. J., and Peck, K. D.: Development of an in situ forming biodegradable poly-lactide-co-glycolide system for the controlled release of proteins, *J. Controlled Rel.* 33: 189–95, 1995.
30. Ravivarapu, H. B., Moyer, K. L., and Dunn, R. L.: Sustained suppression of pituitary-gonadal axis with an injectable, in situ forming implant of leuprolide acetate, *J. Pharm. Sci.* 89: 732–741, 2000.
31. Jain, R. A., Rhodes, C. T., Railkar, A. M., Malick, A. W., and Shah, N. H.: Controlled delivery of drugs from a novel injectable in situ formed biodegradable plga microsphere system, *J. Microencapsulation* 17: 343–362, 2000.
32. Bodmeier, R., and McGinity, J. W.: Solvent selection in the preparation of p1a microspheres prepared by the solvent evaporation method, *International journal of pharmaceutics* 43: 179–186, 1988.
33. Berkland, C., Kim, K., and Pack, D. W.: Fabrication of pig microspheres with precisely controlled and monodisperse size distributions, *J. Controlled Rel.* 73: 59–74, 2001.
34. Shinozaki, J.: Manufacture of microcapsules with concentric double nozzles and apparatus for the process, JP Patent publ. 2001-190943.
35. Lahooti, S., and Sefton, M. J.: Methods for microencapsulation with hema-mma, in Tissue engineering methods and protocols, Morgan, J. R., and Yarmush, M. L., Eds., Humana press inc., Totowa, N.J., 1999, 331–348.
36. Hansen, C. M.: The three dimensional solubility parameter—key to paint component affinities: Ii and iii, *Journal of Paint Technology* 39: 505–514, 1967.
37. Teas, J. P.: Graphic analysis of resin solubilities, Jounal of Paint Technology 40: 19–25, 1968.
38. Barton, A. F. M.: Solubility parameters, *Chemical Reviews* 75: 731–753, 1975.

What is claimed is:

1. A method for preparing an encapsulated composition, comprising:
   providing an aqueous solution composed of water and a core substance dissolved therein;
   providing a polymer solution composed of a water-miscible solvent and a water-insoluble polymer dissolved therein;
   forming a droplet of the aqueous solution containing the core substance using at least one syringe, single nozzle, coaxial nozzle, or microdispenser device; and
   admixing the droplet of aqueous solution with at least a portion of the polymer solution under conditions permitting the water-soluble polymer to deposit as at least one layer on the core substance, thereby affording the encapsulated composition.

2. The method of claim 1, wherein the core substance is a physiologically active substance and the encapsulated composition exhibits controlled release properties.

3. The method of claim 2, wherein the core substance is a protein, oligonucleotide, gene, or polysaccharide.

4. The method of claim 3, wherein the core substance is a protein.

5. The method of claim 1, wherein the water-insoluble polymer is biocompatible.

6. The method of claim 5, wherein the polymer is biodegradable.

7. The method of claim 6, wherein the biodegradable polymer is a homopolymer of lactic acid or glycolic acid or a copolymer of lactic acid and glycolic acid.

8. The method of claim 1, wherein the water-miscible solvent is selected from the group consisting of acetic acid, ethyl acetate, methyl acetate and ethyl formate.

9. The method of claim 1, 2, 3, 4, or 6, wherein said admixing is performed by contacting the droplet of aqueous solution with polymer solution using a coaxial nozzle device.

10. The method of claim 1, 2, 3, 4, or 6, wherein the droplet of aqueous solution is provided with an aqueous protecting layer.

11. The method of claim 1, 2, 3, 4, or 6, wherein said admixing is performed by combining the droplet of aqueous solution with a droplet of the polymer solution to afford a microparticle having an aqueous core and an outer polymer layer.

12. The method of claim 11, further comprising introducing the microparticle into water.

13. The method of claim 1, wherein the water-miscible solvent has a solubility parameter in the range of 16 to 26 $MPa^{1/2}$.

14. The method of claim 1, wherein the water-miscible solvent has a surface tension of less than about 45 mN/m.

15. The method of claim 1, wherein the water-miscible solvent has a water solubility of 5 to 100%.

16. An encapsulated composition made by the method of claim 1, 2, 3, 4 or 6.

* * * * *